United States Patent
Miao et al.

(10) Patent No.: US 9,701,698 B2
(45) Date of Patent: Jul. 11, 2017

(54) SELF-ASSEMBLED MONOLAYERS OF PHOSPHONIC ACIDS AS DIELECTRIC SURFACES FOR HIGH-PERFORMANCE ORGANIC THIN FILM TRANSISTORS

(71) Applicant: THE CHINESE UNIVERSITY OF HONG KONG, Hong Kong (CN)

(72) Inventors: Qian Miao, Hong Kong (CN); Danqing Liu, Hong Kong (CN); Zikai He, Shenzhen (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 14/729,592

(22) Filed: Jun. 3, 2015

(65) Prior Publication Data

US 2015/0364684 A1    Dec. 17, 2015

Related U.S. Application Data

(60) Provisional application No. 62/011,976, filed on Jun. 13, 2014.

(51) Int. Cl.
| | | |
|---|---|---|
| C07F 9/40 | (2006.01) | |
| C07F 9/38 | (2006.01) | |
| H01L 51/05 | (2006.01) | |
| H01L 51/00 | (2006.01) | |

(52) U.S. Cl.
CPC .......... *C07F 9/4018* (2013.01); *C07F 9/3808* (2013.01); *H01L 51/0529* (2013.01); *H01L 51/0046* (2013.01); *H01L 51/0053* (2013.01); *H01L 51/0055* (2013.01); *H01L 51/0094* (2013.01)

(58) Field of Classification Search
CPC ..................... C07F 9/4018; H01L 51/0529
See application file for complete search history.

(56) References Cited

U.S. PATENT DOCUMENTS

2008/0275273 A1    11/2008    Effenberger et al.

FOREIGN PATENT DOCUMENTS

| CN | 1554126 A | 12/2004 |
|---|---|---|
| WO | WO-2014/011935 A1 | 1/2014 |

OTHER PUBLICATIONS

International Search Report dated Jan. 8, 2016 in International Application No. PCT/IB2015/001431, filed Jun. 15, 2015.
Yutaka Ito et al., "Crystalline Ultrasmooth Self-Assembled Monolayers of Alkylsilanes for Organic Field-Effect Transistors", 2009 J. Am. Chem. Soc., Jun. 11, 2009, 131, pp. 9396-9404.
Qin Tang et al., "A Meaningful Analogue of Pentacene: Charge Transport, Polymorphs, and Electronic Structures of Dihydrodiazapentacene", 2009 Chem. Mater, Mar. 19, 2009, 21, pp. 1400-1405.
Yoonyoung Chung et al., "Controlling Electric Dipoles in Nanodielectrics and Its Applications for Enabling Air-Stable n-Channel Organic Transistors", 2011 Nano Letters, Feb. 16, 2011, 11, pp. 1161-1165.
Qin Tang et al., "N-Heteroquinones: Quadruple Weak Hydrogen Bonds and c-Channel Transistors", 2010 Chem. Commun., Mar. 5, 2010, 46, pp. 2977-2979.
Deepak Shukla et al., "Thin-Film Morphology Control in Naphthalene-Diimide-Based Semiconductors: High Mobility n-Type Semiconductors for Organic Thin-Film Transistors", 2008. Chem. Mater, Oct. 27, 2008, 20, pp. 7486-7491.
Danqing Liu et al., "Self-Assembled Monolayers of Phosphonic Acids with Enhanced Surface Energy for High-Performance Solution-Processes N-Channel Organic Thin-Film Transistors", 2013, May 3, 2013, 52, pp. 6222-6227.
Zhixiong Liang et al., "Soluble and Stable N-Heteropentacenes with High Field-Effect Mobility", 2011, Advanced Materials, Feb. 9, 2011, 23, pp. 1535-1539.
Sung Kyu Park et al., "High Mobility Solution Processed 6, 13-Bis(Triisopropyl-Silylethynyl) Pentacene Organic Thin Film Transistors", 2007, Applied Physics Letters, Aug. 9, 2007, 91, pp. 063514(1)-063514(3).
Ying Diao et al., "Solution Coating of Large-Area Organic Semiconductor Thin Films with Aligned Single-Crystalline Domains", 2013 Nature Materials, Jun. 2, 2013, 12, pp. 665-671.
Yaorong Su et al., "Low-Voltage Organic Field-Effect Transistors (OFETs) with Solution-Processed Metal-Oxide as Gate Dielectric", 2011 Applied Materials & Interfaces, Oct. 19, 2011, pp. 4662-4667.
S.Kobayashi et al., "Fabrication and Characterization of C 60 Thin-Film Transistors with High Field-Effect Mobility", 2003 Applied Physics Letters, Apr. 4, 2003, 82, pp. 4581-4583.
Thomas D. Anthopoulos et al., "High Performance N-Channel Organic Field-Effect Transistors and Ring Oscillators Based on C 60 Fullerene Films", 2006 Applied Physics Letters, Nov. 20, 2006, 89, pp. 213504(1)-213504(3).

*Primary Examiner* — Golam M M Shameem
(74) *Attorney, Agent, or Firm* — Saliwanchik, Lloyd & Eisenschenk

(57) ABSTRACT

Cycloalkylalkylphosphonic acids are presented that are useful for forming a self-assembled monolayer (SAM) on a surface of a metal oxide layer. The combined SAM and metal oxide layer form the dielectric layer of an organic thin film transistor (OTFT). The OTFT can be formed with p-type and n-type organic semiconductor layers on the SAM. The OTFT display superior field effect mobilities and air stabilities to other SAMs and the SAMS of cycloalkylalkylphosphonic acids allow deposition of the organic semiconductors by either vapor deposition or solution processing techniques.

10 Claims, 5 Drawing Sheets

SELF-ASSEMBLED MONOLAYERS OF PHOSPHONIC ACIDS AS DIELECTRIC SURFACES FOR HIGH-PERFORMANCE ORGANIC THIN FILM TRANSISTORS

CROSS-REFERENCE TO RELATED APPLICATION

This application claims the benefit of U.S. Provisional Application Ser. No. 62/011,976, filed Jun. 13, 2014, the disclosure of which is hereby incorporated by reference in its entirety, including all figures, tables and drawings.

BACKGROUND OF INVENTION

Light-weight, flexible, and low-cost organic electronic devices are a growing market. Organic light emitting diode (OLED) displays for smart phones have been commercialized. Organic thin film transistors (OTFTs) are basic units in organic integrated circuits and are an important elemental organic electronic device. For example, these elements are employed in radio-frequency identification (RFID) tags and sensors and are used to drive individual pixels of active matrix displays. Low-power complementary circuits use positive and negative gate voltages to switch transistors, requiring p- and n-channel transistors. However, n-channel OTFTs are underdeveloped relative to their p-channel counterparts. N-channel OTFTs suffer from poor stability in air. Typically, two methods are used to fabricate OTFTs, namely, vacuum deposition and solution processing. Vacuum deposition techniques are more expensive to perform than are solution processes that are compatible with roll-to-roll or ink jet printing techniques for large area deposition on flexible substrates. Field effect mobility is the most important parameter for OTFTs, and OTFTs with high field effect mobility have wide applications. For example, OTFTs with field effect mobility higher than 1 $cm^2V^{-1}s^{-1}$ can be used to replace thin film transistors of amorphous silicon.

An OTFT typically consists of three electrodes (gate, drain, and source), a dielectric layer, and an organic semiconductor layer. OTFTs are interface devices whose performance strongly depends on the interface between an organic semiconductor and a dielectric regardless of the manner that the organic semiconductor is fabricated, whether by vacuum-deposition or solution-processing. Therefore, it is crucially important to control the structures and properties of the dielectric surface of the OTFT during device fabrication. Hence, to achieve OTFTs that exhibit high field effect mobility and robust environmental stability, there remains a need to develop a general dielectric surface for high-performance p- and n-channel OTFTs that can be fabricated using either vacuum deposition or solution processing.

BRIEF SUMMARY

Embodiments of the invention are directed to cycloalkylalkylphosphonic acids and their preparation via an intermediate dialkyl cycloalkylalkylphosphonate ester. Another embodiment of the invention is directed to self-assembled monolayer (SAM) of the cyclohexyldodecylphosphonic acid formed on a surface. The surface can be that of a metal oxide dielectric. Another embodiment of the invention is directed to an organic thin film transistor that includes a dielectric comprising the metal oxide layer with a SAM of the cyclohexyldodecylphosphonic acid. The SAM permits the deposition of n-type and p-type organic semiconductors by either vapor deposition or solution processing methods to form OTFTs that display high field effect mobilities and good air stability.

DETAILED DISCLOSURE

Embodiments of the invention are directed to cycloalkylalkylphosphonic acids, which have been discovered to provide superior performance when applied as self-assembled monolayers (SAMs) on dielectric layer of organic thin film transistors (OTFTs). Cycloalkylalkylphosphonic acids permit the formation of general dielectric surfaces for OTFTs that display high field effect mobilities, good air stabilities at low operating voltages, and are amenable for use with solution-processed and vacuum-deposited n-type and p-type organic semiconductors. A cycloalkylalkylphosphonic acid consists of a linear alkyl chain that is α-substituted by a phosphonic acid group and ω-substituted with a cycloalkyl group, selected from cyclopentanyl, cyclohexyl, cycloheptyl, and cyclooctyl. Having the structure:

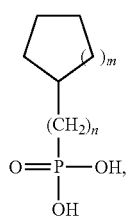

where n is 6 to 20 and m is 1 to 4. The cycloalkylalkylphosphonic acid can be formed from a dialkyl cycloalkylalkylphosphonate ester:

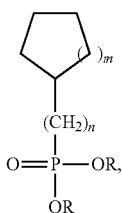

where n is 6-20, m is 1 to 4, and R is methyl, ethyl, or propyl.

Figure 1:
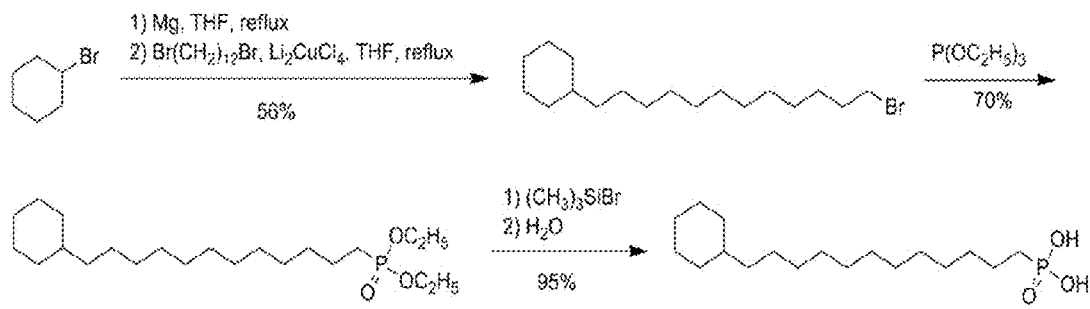
FIG. 1 shows the preparation of cyclohexyldodecylphosphonic acid (CDPA) via a multistep synthesis through a dialkyl cycloalkylalkylphosphonate ester, according to an embodiment of the invention.

In an embodiment of the invention, the cycloalkylalkylphosphonic acid is prepared by a sequence of reactions, starting from a coupling between an α,ω-dihalogen substituted n-alkane and a Grignard reagent, a cycloalkylmagnesium halide, formed from a halogen substituted cycloalkane to yield an α-halo-ω-cycloalkylalkane. The halogen can be a chloride, bromide, or iodide. The n-alkane can be n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, or n-icosane. After isolation, the α-halo-ω-cycloalkylalkane is combined with a trialkyl phosphite at a sufficient temperature for a sufficient time to form a dialkyl cycloalkylalkylphosphonate by a Michaelis-Arbuzov reaction. The trialkyl phosphite can have any alkyl group, for example, methyl, ethyl, or propyl. The dialkyl cycloalkylalkylphosphonate is combined with trimethylsilicon bromide and subsequently water to form the cycloalkylalkylphosphonic acid. The multistep reaction is illustrated in FIG. 1 for the preparation of cyclohexyldodecylphosphonic acid (CDPA).

In an embodiment of the invention, the cycloalkylalkylphosphonic acid forms a SAM on the surface of a metal oxide. Phosphonic acids appear to bind to a metal oxide surface by first coordinating of the phosphoryl oxygen to Lewis acidic sites on the surface, followed by condensation of the P—OH groups with surface hydroxyl groups or other surface oxygen species. Advantageously, the formation of multilayers does not occur, as polymerization of phosphonic acids does not occur, unlike silanes and other compounds commonly employed to form monolayers on metal oxides. Because these phosphonic acids are stable toward water, anhydrous conditions are not necessary for the formation of SAMs. These phosphonic acids monolayers have an ambient stability for long periods of time. The metal oxide can be, but is not limited to, aluminum oxide, titanium oxide, zirconium oxide, planar mica, silica, zinc oxide, copper oxide, nickel oxide, tantalum oxide, hafnium oxide, iron oxide, chromium oxide, niobium oxide, zirconium oxide, or any mixed metal oxide thereof. A monolayer of these phosphonic acids on the metal oxide surface can be prepared by contacting the metal oxide with a solution of the cycloalkylalkylphosphonic acid, generally, but not necessarily, a dilute solution for a sufficient period of time, followed by rinsing with a solvent for unbound cycloalkylalkylphosphonic acid and drying the surface, for example, under a stream of an inert gas. The SAM can be formed from a single cycloalkylalkylphosphonic acid or can be formed from a mixture of cycloalkylalkylphosphonic acids having different n and m values.

Figure 2:
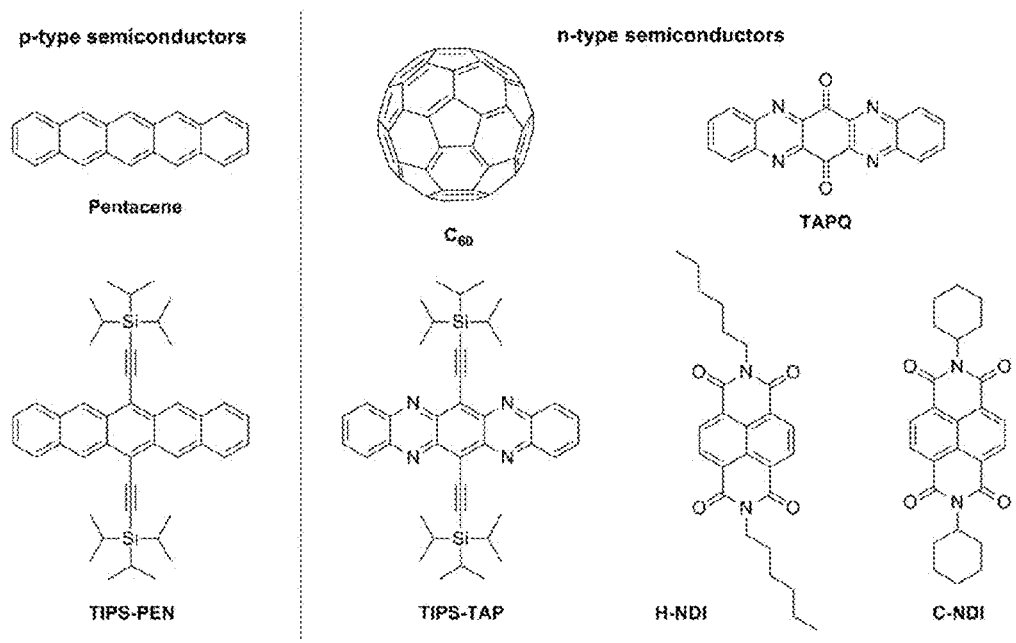
FIG. 2 shows various n-type and p-type organic semiconductors that can be deposited on a self-assembled monolayer (SAM) of a cyclohexyldodecylphosphonic acid of a dielectric layer to form an organic thin film transistor (OTFT), according to an embodiment of the invention.
Figure 3:
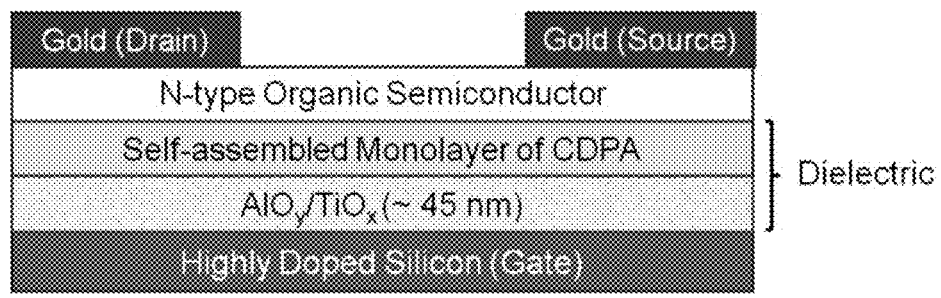
FIG. 3 shows the structure of an exemplary (OTFT) according to an embodiment of the invention.

In an embodiment of the invention, an organic thin film transistor (OTFT) is formed that comprises a cycloalkylalkylphosphonic acid SAM coated metal oxide as the dielectric layer. For example, a gate can be formed from a highly doped Si substrate, upon which a metal oxide dielectric can be deposited by any known technique, including, chemical vapor deposition (CVD), atomic layer deposition (ALD), and solution-processing, for example, using sol-gel precursors compatible with roll-to-roll and inkjet printing techniques. The metal oxide dielectric layer with the cycloalkylalkylphosphonic acid SAM can be formed by contacting a solution of the cycloalkylalkylphosphonic acid with the metal oxide layer. An organic semiconductor layer is deposited on the cycloalkylalkylphosphonic acid SAM of the dielectric layer. The organic semiconductor can be formed by vacuum deposition, or by solution processing. The organic semiconductor can be a p-type semiconductor, including, but not limited to, pentacene and 6,13-bis((triisopropylsilyl)ethynyl)-pentacene (TIPS-PEN), or an n-type semiconductor, including, but not limited to, buckminsterfullerenes ($C_{60}$ or $C_{70}$), 6,13-bis((triisopropylsilyl)ethynyl)-5,7,12,14-tetraazapentacene (TIPS-TAP), 5,7,12,14-tetraaza-6,13-pentacenequinone (TAPQ), N,N'-dihexyl-1,4,5,8-naphthalene-tetracarboxydimide (H-NDI), and N,N'-dicyclohexyl-1,4,5,8-naphthalene-tetracarboxydimide (C-NDI). Other organic semiconductors include: rubrene, tetracene, diindenoperylene, perylenediimides, tetracyanoquinodimethane (TCNQ), poly(3-hexylthiophene) (P3HT)), polyfluorene, polydiacetylene, poly(2,5-thienylene vinylene), poly(p-phenylene vinylene) (PPV), diketopyrrolopyrroles (DPPs), or any other n-type or p-type semiconductor can be deposited on the cycloalkylalkylphosphonic acid SAM layer metal oxide dielectric. The structures for some of these organic semiconductors are given in FIG. 2. Source and drain electrodes can be formed on the organic semiconductor layer to complete the field-effect transistor. For example, gold electrodes can be deposited by a vapor deposition technique through a shadow mask. An exemplary OTFT configuration is shown in FIG. 3 where a substrate that acts as the gate electrode is covered by a metal oxide dielectric layer, a cycloalkylalkylphosphonic acid SAM, and an organic semiconductor layer, upon which source and drain electrodes are supported.

The general applicability of the CDPA modified $AlO_y$/$TiO_x$, p- and n-channel OTFTs can be appreciated from exemplary OTFTs, according to an embodiment of the invention, prepared with two p-type semiconductors and two n-type semiconductors using vacuum deposition or solution-based methods. Pentacene and $C_{60}$ are vacuum-deposited semiconductors and 6,13-bis((triisopropylsilyl)ethynyl)-pentacene (TIPS-PEN) and 6,13-bis((triisopropylsilyl)ethynyl)-5,7,12,14-tetraazapentacene (TIPS-TAP) are solution-processed semiconductors, all of which possess very high field effect mobilities. The excellent properties afforded by the CDPA can be appreciated in light of SAMs prepared from CDPA and 4-cyclohexylbutylphosphonic acid (CBPA), which is a homologue of CDPA but with a shorter alkyl chain, and octadecylphosphonic acid (OPA), a well studied phosphonic acids for OTFTs, which has an alkyl chain with the same number of carbon atoms as CDPA but lacks a cycloalkyl end unit. CBPA is readily synthesized by the method used to prepare CDPA, as indicated below. The SAMs of CDPA and CBPA form on the surface of $AlO_y$/$TiO_x$ in a very similar way to that practiced for preparation of SAMs of phosphonic acids on the identical metal oxides. SAM-modified $AlO_y$/$TiO_x$ can be characterized with respect to molecular ordering in the SAMs and with respect to the surface and electrical properties related to its role as a dielectric layer in OTFTs.

Figure 5:
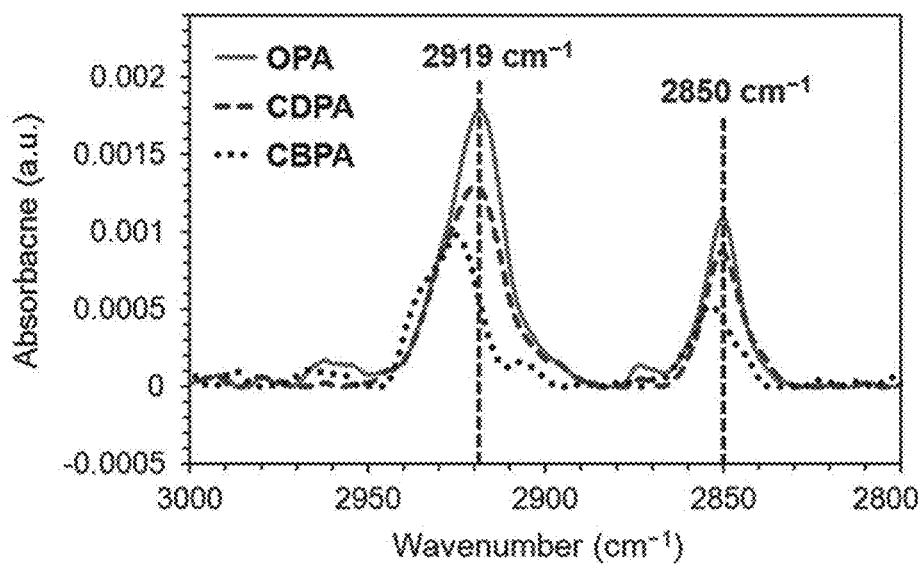
FIG. 5 shows a portion of the grazing angle attenuated total reflection Fourier transform infrared (GATR-FTIR) spectra of SAMs of OPA, CDPA and CBPA, according to an embodiment of the invention.

Although the cyclohexyl terminal group in CDPA is larger than the methyl terminal group in well-studied long-alkyl chain SAMs, a highly ordered monolayer is formed on the surface of $AlO_y/TiO_x$. SAMs of CDPA, CBPA, and OPA are probed by using grazing angle attenuated total reflection Fourier transform infrared (GATR-FTIR) spectroscopy and Near-edge X-ray absorption fine structure (NEXAFS) spectroscopy, as shown in FIG. 5. GATR-FTIR spectra of the SAMs of CDPA and OPA exhibit two peaks at 2850 $cm^{-1}$ and 2919 $cm^{-1}$, which are attributed to the symmetric (vs) and asymmetric (vas) stretching modes of $CH_2$ groups, respectively, that can be used as a reference, for well ordered alkyl chains within a SAM.

The C—H stretches for the SAM of CBPA shift to larger wavenumbers, 2854 and 2925 $cm^{-1}$ for vs and vas, respectively. This shift is similar to that observed in the IR spectra of phosphonic acid SAMs with shorter straight alkyl chains, and is an indicator of disordered SAMs. NEXAFS spectroscopy qualitatively assesses the structural order in SAMs with a high-intensity, monochromatic, and linearly-polarized X-ray from a synchrotron source to measure electronic transitions near the absorption edge of an atom. Analyses of the electronic transitions near the carbon K-edge are commonly used to characterize the ordering of long-chain alkyl groups in SAMs. X-ray absorption spectra of the SAMs of CDPA, CBPA and OPA, collected at varied angles of incidence (θ) allow probing of the SAMs' order. The NEXAFS spectra, at 90° and 25° X-ray incidence angles, exhibit an angle dependence (i.e., difference spectra intensity) at a peak related to σ*C—H (ca. 287.5 eV) for the SAMs of CDPA and OPA. In contrast, the SAM of CBPA does not exhibit angle dependence using the same analysis. Again, consistent with the results from GATR-FTIR, SAMs of OPA and CDPA form well-ordered monolayers while CBPA forms a disordered monolayer, since transitions to C—C and C—H antibonding orbitals (e) are known to depend on the alignment of the linearly polarized light with the antibonding orbital in relation to the orientation of alkyl chains in the SAMs.

Figure 6:
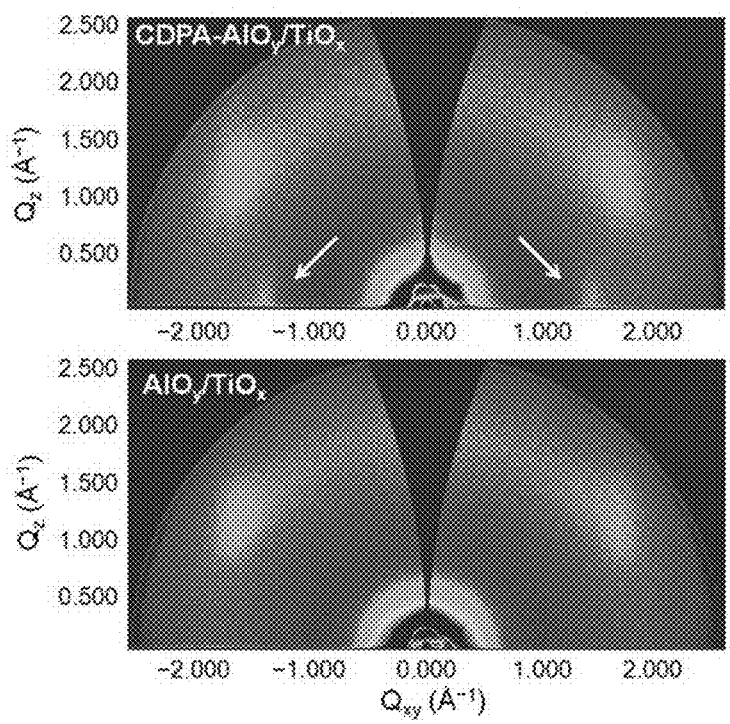
FIG. 6 shows grazing incidence X-ray diffraction (GIXD) patterns of CDPA-modified $AlO_x/TiO_x$, according to an embodiment of the invention, and bare $AlO_x/TiO_x$ where the arrows indicate the diffraction peak from the SAM.

An ordered monolayer of CDPA, according to an embodiment of the invention, is crystalline, as is evident for the SAM of CDPA using grazing incidence X-ray diffraction (GIXD) when exposing the thin films to high-intensity synchrotron X-rays at a very shallow incident angle (ca. 0.12°), where the X-ray intensity is focused into a region immediately above the substrate, for sensitivity to out-of-plane (perpendicular to the substrate) and in-plane periodic structures of the very thin films. As shown in FIG. 6, the GIXD patterns from the SAM of CDPA exhibit a Bragg rod at $Q_{xy}=1.41$ $Å^{-1}$, which indicates the SAM is crystalline with a lattice constant of 4.45 Å. The appearance of only one Bragg rod in the detection range suggests that the SAM has a hexagonal lattice. The lattice constant is larger than that of the OPA SAM (4.2 Å) by only 6%, suggesting a close packing of bulky cyclohexyl terminal groups.

For application in OTFTs as a dielectric, CDPA-modified $AlO_y/TiO_x$ require appropriate surface roughness, surface energy, capacitance and leakage current. As determined using atomic force microscopy (AFM), CDPA formed very smooth surface with a root mean square (RMS) roughness of 0.2 nm over an area of 25 $μm^2$. This roughness is comparable to that of the ultra-smooth SAM of octadecyltrimethoxysilane (OTMS) on $SiO_2$, as reported in Ito et al., *J. Am. Chem. Soc.* 2009, 131, 9396. The surface energy of the SAM of CDPA is 31.6 mN $m^{-1}$ containing a polar component of 0.3 mN $m^{-1}$ and a dispersion component of 31.3 mN $m^{-1}$. The SAM of CDPA has a larger surface energy than that of OPA (26.6 mN $m^{-1}$) by increasing the dispersion component while keeping the polar component almost unchanged. This is in agreement with the fact that CDPA contains a non-polar cyclohexyl terminal group, which has a larger area of contact than the methyl terminal group in OPA. Due to the enhanced surface energy, the CDPA-modified $AlO_y/TiO_x$, according to an embodiment of the invention, exhibits much better wettability than the OPA-modified $AlO_y/TiO_x$ and is completely wettable by a variety of organic solvents, such as chloroform, isopropyl alcohol, ethyl acetate and toluene, with a static contact angle smaller than 5°. This good wettability readily allows identification of optimize solvents for use during drop casting. In comparison, the SAM of CBPA exhibited a larger surface energy of 36.7 mN $m^{-1}$ with a polar component of 1 mN $m^{-1}$ and a dispersion component of 35.7 mN $m^{-1}$. The larger surface energy of CBPA is likely due to disordered shorter alkyl chains, which allow the probe liquids to achieve greater interaction with the metal oxides under the SAM. The capacitance per unit area (Ci) of CDPA- and CBPA-modified $AlO_y/TiO_x$ measures 210±18 and 240±16 nF $cm^{-2}$, respectively. The capacitance varies slightly among different devices because spin-coating process does not yield an $AlO_y/TiO_x$ layer of uniformed thickness. The leakage current through the CDPA-modified $AlO_y/TiO_x$ was about $1.6×10^{-6}$ A $cm^{-2}$ as measured from a metal-insulator-metal structure with a voltage of 3 V. In comparison to the CDPA-modified $AlO_y/TiO_x$, the OPA-modified $AlO_y/TiO_x$ has essentially the same leakage current, while the CBPA-modified $AlO_y/TiO_x$ has a larger leakage current ($3.4×10^{-6}$ A $cm^{-2}$ with the same voltage). The larger capacitance and leakage current of the CBPA-modified $AlO_y/TiO_x$ appear to be related to the shortness of the alkyl chain of CBPA.

Figure 7:
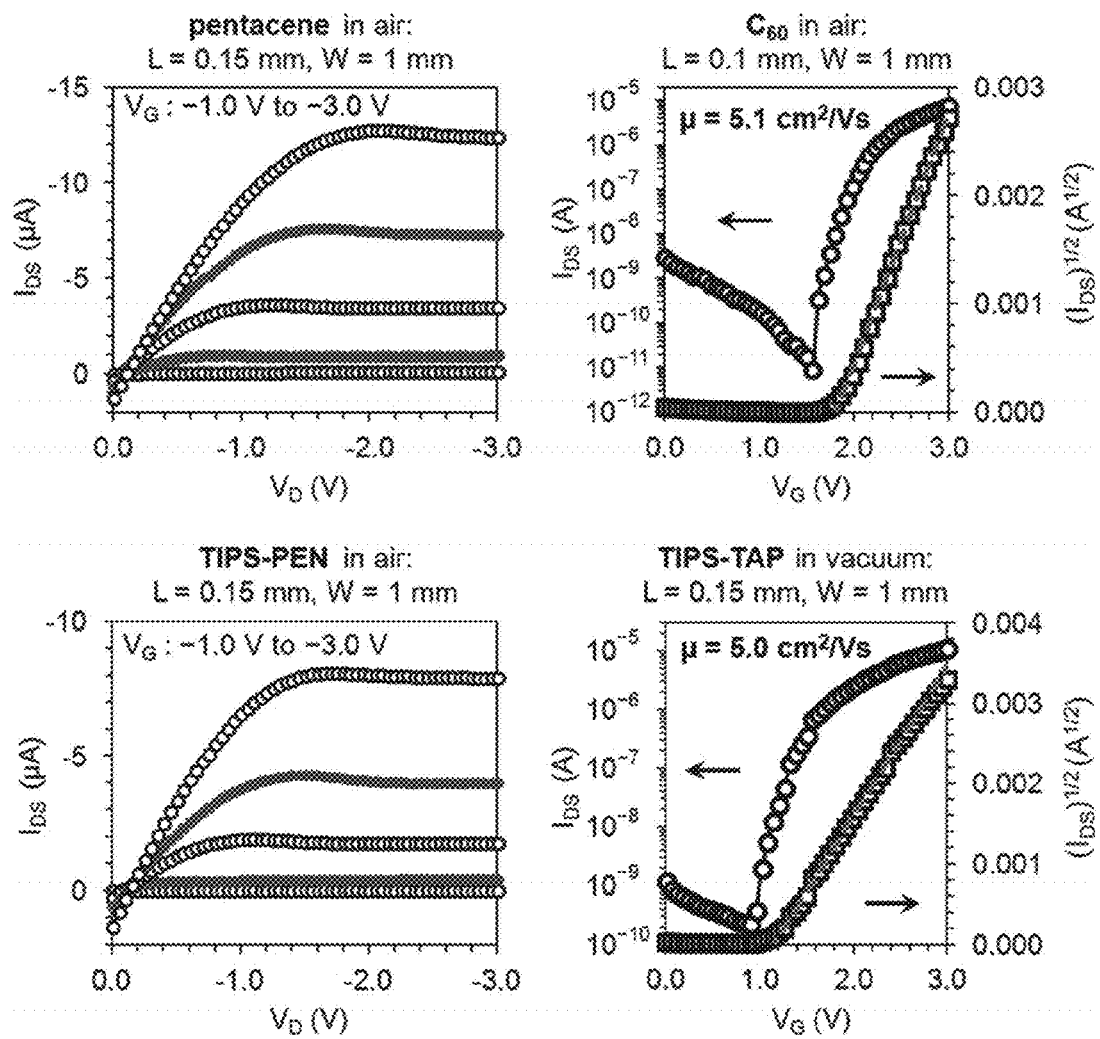
FIG. 7 shows output I-V curves for the OTFTs of pentacene and TIPS-PEN on CDPA-modified $AlO_x/TiO_x$ with varied gate voltage (VG) and the transfer I-V curves for the OTFTs of $C_{60}$ and TIPS-TAP on the CDPA-modified $AlO_x/TiO_x$ as measured at a constant drain voltage (VD) of 3.0 V.

OTFTs of pentacene and $C_{60}$, according to an embodiment of the invention, are fabricated by vacuum-deposition of these organic semiconductors on CDPA- and OPA-modified $AlO_y/TiO_x$, and OTFTs of TIPS-PEN and TIPS-TAP, according to an embodiment of the invention, are fabricated by drop-casting solutions of the corresponding organic semiconductors onto CDPA-modified $AlO_y/TiO_x$. Exemplary OTFTs have top-contact gold as drain and source electrodes. Because OPA-modified $AlO_y/TiO_x$ is poorly wetted by most common organic solvents, drop-casting cannot result in the deposition of a high-quality thin film. Therefore solution-processed OTFTs of TIPS-PEN and TIPS-TAP are not fabricated on the OPA-modified $AlO_y/TiO_x$. With a large capacitance per unit area (Ci), the OTFTs operate at a gate voltage as low as 3 V. The OTFTs on CDPA- and OPA-modified $AlO_y/TiO_x$ exhibit essentially the same threshold voltage. The field-effect mobilities of OTFTs on the CDPA- and OPA-modified $AlO_y/TiO_x$, as measured in vacuum and in air, are summarized in Table 1, below, where average value were obtained from at least 20 channels on five different substrates. The typical output and transfer I-V curves of the best-performing OTFTs on the CDPA-modified $AlO_y/TiO_x$ are shown in FIG. 7. Substituting CBDA for CDPA, results in inferior OTFTs, where the vacuum-deposited OTFTs of pentacene and $C_{60}$ exhibit lower field-effect mobility of 1.6±0.2 $cm^2$ $V^{-1}$ $s^{-1}$ (measured in air) and 0.021±0.005 $cm^2$ $V^{-1}$ $s^{-1}$ (measured in vacuum), respectively, and the solution-processed OTFTs of TIPS-PEN and TIPS-TAP exhibit lower field effect mobility of 0.23±0.07 cm2 V-1 s-1 (measured in air) and (7.3±0.6)×10-3 cm2 V-1 s-1 (measured in vacuum), respectively. CDPA-modified $AlO_y/TiO_x$ constructed with other organic semiconductors, including copper phthalocyanine, N,N'-dicyclohexyl-1,4,5,8-naphthalene-tetracarboxydimide (C-NTCDI) and N,N'-dihexyl-1,4,5,8-naphthalene-tetracarboxydimide (H-NTCDI), The vacuum-deposited OTFTs of C-NTCDI and solution-processed OTFTs of H-NTCDI on CDPA-modified $AlO_y/TiO_x$ are air stable with high field effect mobilities of 1.50±0.30 and 1.09±0.26 cm2 V-1 s-1, respectively.

TABLE 1

Field-effect mobilities ($cm^2$ $V^{-1}$ $s^{-1}$) of OTFTs fibricated on CDPA- and OPA-modified $AlO_y/TiO_x$ as tested in vacuum (Vac.) or in air.

| | pentacene | | $C_{60}$ | | TIPS | TIPS-TAP |
| | CDPA | OPA | CDPA | OPA | CDPA | CDPA |
|---|---|---|---|---|---|---|
| Vac. | | | 3.08 ± 0.93 highest: 5.5 | 0.93 ± 0.25 highest: 1.2 | | 2.57 ± 0.89 highest: 5.0 |
| Air | 3.86 ± 0.47 highest: 5.7 | 2.21 ± 0.46 highest: 2.9 | 2.98 ± 0.83 highest: 5.1 | 0.66 ± 0.28 highest: 1.1 | 1.64 ± 0.55 highest: 2.7 | 0.78 ± 0.32 highest: 1.44 |

The field effect mobilities of pentacene and $C_{60}$, as measured from their OTFTs on the SAM of CDPA, are among the highest values for the two benchmark organic semiconductors. In comparison to the SAM of CDPA, the crystalline SAM of octadecyltrimethoxysilane (OTMS) has higher field effect mobility for vacuum-deposited OTFTs of C60 (4.7±0.41 $cm^2$ $V^{-1}$ $s^{-1}$ when measured in an atmosphere of $N_2$) but lower field-effect mobility for pentacene (2.8±0.2 $cm^2$ $V^{-1}$ $s^{-1}$), as disclosed in Ito et al., *J. Am. Chem. Soc.* 2009, 131, 9396. The maximum field-effect mobility of the TIPS-PEN OTFTs on the SAM of CDPA (2.7 $cm^2$ $V^{-1}$ $s^{-1}$) is higher than the reported maximum mobility from solution-processed unstrained films of TIPS-PEN (1.8 $cm^2$ $V^{-1}$ $s^{-1}$) by Park et al., *Appl. Phys. Lett.* 2007, 91, 063514, but lower than that from strained single-crystalline films (11 $cm^2$ $V^{-1}$ $s^{-1}$), of Diao et al. *Nat. Mater.* 2013, 12, 665. The electron mobility of TIPS-TAP OTFTs on the SAM of CDPA (5.0 $cm^2$ $V^{-1}$ $s^{-1}$) appears to be the highest among solution-processed polycrystalline n-channel OTFTs. In comparison to the SAM of 12-methoxydodecylphosphonic acid (MODPA) reported in Liu et al., *Angew. Chem. Int. Ed.* 2013, 52, 6222, which has a methoxyl terminal group to enhance surface energy for high-mobility solution-processed n-channel OTFTs, the SAM of CDPA has a greater average field effect mobility by about 50% and displays a significantly improved air stability of the n-channel OTFTs of TIPS-TAP. It appears that the improved air stability is due to a lack of the oxygen atom from the SAM surface where polar oxygen atoms allow accumulate water at the semiconductor-dielectric interface, as SAMs of MODPA and CDPA exhibit water contact angle of 75.2° and 99.8°, respectively. The cyclohexyl group of CDPA allows a SAM that is hydrophobic and organic-solvent-wettable, which is a critical for fabricating air-stable solution-processed n-channel OTFTs.

Figure 8:
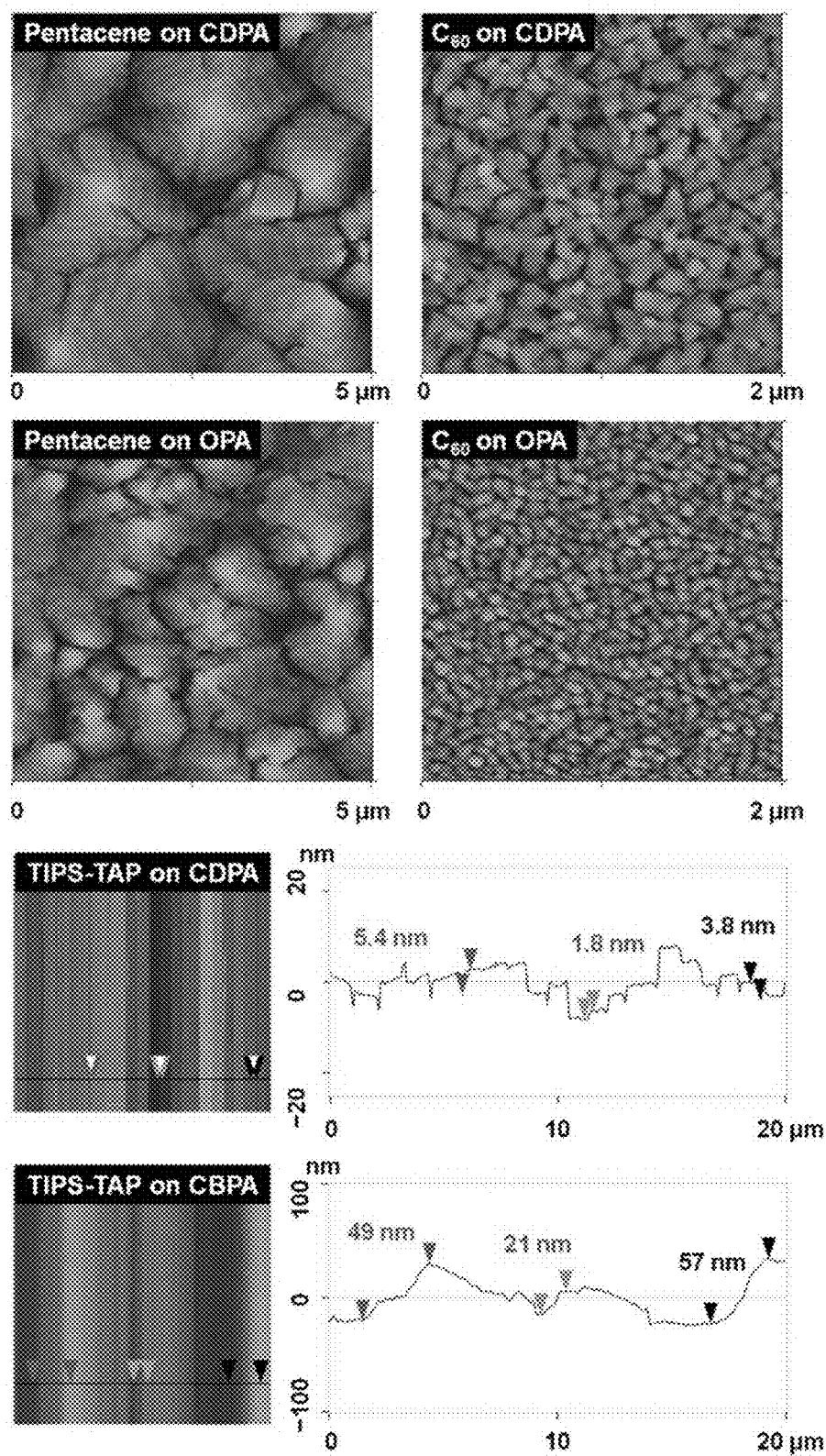
FIG. 8 shows atomic force microscopy (AFM) height images of thin films of pentacene, $C_{60}$ and TIPS-TAP deposited on different SAMs.

Vacuum-deposited films of the organic semiconductors on the SAMs of CDPA and OPA were studied with. The X-ray diffractions from vacuum-deposited films of pentacene on the SAMs of CDPA and OPA are essentially the same by x-ray diffraction (XRD) and atomic force microscopy (AFM), exhibiting four diffraction peaks in accordance with a thin-film phase of pentacene. As indicated in the AFM images shown in FIG. 8, the pentacene films deposited on the SAMs of CDPA and OPA are composed of grains with distinct terraces. The grains in the films on CDPA, with a size over 1 μm, are larger than those in the films on OPA, presumably because layer-by-layer growth is favored by the SAM of CDPA that displays a higher surface energy. Therefore, the difference in mobility of pentacene OTFTs on different SAMs can be attributed to the difference of film morphology. In agreement with the different film morphologies on the SAMs of CDPA and OPA, AFM images of very thin (3 nm thick) films reveal that the film of pentacene on CDPA has a higher coverage with less grain boundaries. The film of $C_{60}$ on the SAM of CDPA exhibits two X-ray diffraction peaks at 2θ=10.86° (d spacing=8.19 Å) and 2θ=21.78° (d spacing=4.08 Å), which are in agreement with the (111) and (222) diffractions as derived from the single crystal structures. This indicates a crystalline film, in which the (111) plane is parallel to the surface. In contrast, the film of $C_{60}$ deposited on the SAM of OPA under the same condition exhibits only one small diffraction peak at 2θ=10.86°, which indicates a film of apparently lower crystallinity. Unlike the $C_{60}$ films grown on the SAM of CDPA, polycrystalline films of $C_{60}$ grown by molecular-beam deposition, as reported in Kobayash et al. *Appl. Phys. Lett.* 2003, 82, 4581, or hot wall epitaxy growth, as reported in. Anthopoulos et al. *Appl. Phys. Lett.* 2006, 89, 213504, exhibit X-ray diffraction peaks at 2θ=10.8°, 17.8°, and 20.9°, which corresponded to the (111), (220) and (311) planes, respectively, which is indicative of films containing crystalline domains aligned in different directions. Hence, the SAM of CDPA, according to an embodiment of the invention, is able to initiate growth of a highly crystalline film of $C_{60}$ with unidirectional molecular alignment very possibly because of a quasi-expitaxy growth. Vacuum-deposited films of $C_{60}$ on the disordered SAM of CBPA are amorphous and exhibit low mobility, presumably due to lack of quasi-epitaxy growth. As displayed in the AFM images of FIG. 8, the 40 nm-thick $C_{60}$ films on the SAM of OPA is composed of irregularly round grains with diameters of tens of nanometers, which are typical for vacuum-deposited $C_{60}$, and appear to be associated with an island growth mode. The film on the SAM of CDPA contains flat crystallites of hundreds of nanometers long and wide. Each of the crystallites is, presumably, grown by a layer-by-layer mode in agreement with the higher surface energy of the SAM of CDPA. Therefore, the high mobility of the $C_{60}$ films on the SAM of CDPA appears to be due to the combination both high crystallinity and good morphology that results from the crystalline nature and higher surface energy of the SAM.

Drop-cast films of TIPS-TAP on the SAMs of CDPA and CBPA are crystalline as indicated by the similar XRD patterns from these films. Differences between the two films are revealed by the AFM images shown in FIG. 8. The drop-cast film of TIPS-TAP on the SAM of CDPA contains highly ordered flat micro-stripes of about 1 μm wide, while the film on the SAM of CBPA exhibits a much rougher surface, which suggests lower ordering at the micrometer scale. As the CBPA SAM is disordered in nature, the ordering of SAMs appears to determine the morphology and molecular ordering for solution-processed films. A crystalline SAM that is wettable by a variety of organic solvents appears to be optimal for solution-processed OTFTs.

Methods and Materials

1-Bromo-12-cyclohexyl-dodecane

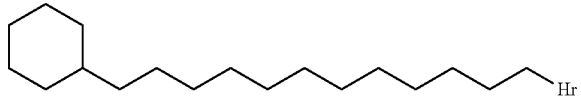

A reaction mixture of 0.35 g of magnesium and 1.5 ml (12 mmol) of bromocyclohexane were formed in 25 mL of anhydrous THF, and the reaction mixture was refluxed under a nitrogen atmosphere for 2 hours. The resulting solution of cyclohexylmagnesium bromide was cooled to room temperature. The salts $CuCl_2$, 0.134 g (1 mmol), and LiCl (0.085 g 2 mmol) were dissolved in 10 mL of THF to form an orange-red solution of $Li_2CuCl_4$ (0.1M). To a solution of 1,12-dibromododecane (3.26 g, 10 mmol) in 5 mL anhydrous THF under nitrogen was added 2 mL of the 0.1M solution of $Li_2CuCl_4$. The resulting solution was cooled to 0° C. and was added dropwise to the solution of cyclohexylmagnesium bromide (12 mmol) in THF using a dropping funnel over a 20 min period. The reaction mixture was stirred for 20 hours at room temperature under nitrogen and treated with 10 mL of 1M $NH_4Cl$ aqueous solution. The resulting mixture was extracted with 20 mL of ethyl acetate. The organic solution was washed twice with a saturated NaCl aqueous solution, dried with anhydrous $Na_2SO_4$, and concentrated under reduced pressure. The crude product was purified by silica gel column chromatography using hexane as the eluent to yield 1.85 g (56%) 1-bromo-12-cyclohexyl-dodecane as a colorless oil. $^1$H NMR ($CDCl_3$) δ (ppm): 3.38 (t, J=6.8 Hz, 2H), 1.82~1.89 (m, 2H), 1.62~1.70 (m, 5H), 1.40~1.42 (m, 2H), 1.15~1.26 (m, 22H), 0.81~0.89 (m, 2H). $^{13}$C NMR ($CDCl_3$) δ (ppm): 37.8, 37.7, 34.1, 33.62, 33.0, 30.2, 29.9, 29.82, 29.79, 29.7, 29.6, 28.9, 28.3, 27.0, 26.9, 26.6. HRMS (API+) Calcd. for $C_{18}H_{35}Br$ $[M+H]^+$: 330.1917. Found: 330.1910.

Diethyl 12-cyclohexyldodecylphosphonate

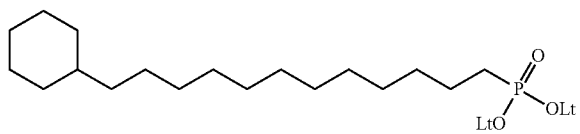

A mixture of 2 mL (12 mmol) of triethyl phosphite and 1.13 mg (3.4 mmol) of 1-bromo-12-cyclohexyl-dodecane were heated at 160° C. for 2 days with continuous stirring under nitrogen. After removal of excessive triethyl phosphite at 100° C. under reduced pressure, the residue was purified by silica gel column chromatography using ethyl acetate/hexane (1:1) as the eluent yielding 840 mg (70%) of diethyl 12-cyclohexyldodecylphosphonate as a colorless oil. $^1$H NMR ($CDCl_3$) δ (ppm): 4.01~4.06 (m, 4H), 1.55~1.69 (m, 9H), 1.11~1.28 (m, 30H), 0.78~0.80 (m, 2H). $^{13}$C NMR ($CDCl_3$) δ (ppm): 61.3 (d, $^2J_{C-P}$=6.4 Hz), 37.7, 37.6, 33.5, 30.6 (d, $^3J_{C-P}$=16.8 Hz), 30.0, 29.76, 29.71, 29.69, 29.64, 29.4, 29.1, 26.9, 26.8, 26.5, 25.0 (d, $^1J_{C-P}$=139.4 Hz), 22.4 (d, $^2J_{C-P}$=5.2 Hz), 16.5 (d, $^3J_{C-P}$=6.0 Hz). HRMS (API+) Calcd. for $C_{22}H_{45}O_3P$ $[M+Na]^+$: 411.2999. Found: 411.3007.

12-Cyclohexyldodecylphosphonic acid (CDPA)

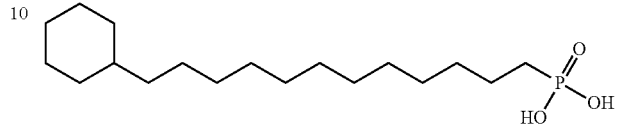

Trimethylsilylbromide, 0.3 mL (2.4 mmol), was added to 600 mg (1.5 mmol) of diethyl 12-cyclohexyldodecylphosphonate in 2 mL of anhydrous $CH_2Cl_2$ at 0° C. under nitrogen. The reaction mixture was stirred under nitrogen overnight at room temperature. After addition of 5 mL of water, the reaction mixture was stirred for 2 hours. The solvents ($CH_2Cl_2$ and water) were evaporated under a flow of compressed air overnight to yield a white powder. The white powder was washed with hexane in a funnel to yield 475 mg (95%) of 12-cyclohexyldodecylphosphonic acid as white solids. Melting point: 90~92° C. $^1$H NMR (DMSO-$d_6$) δ (ppm): 5.32 (br s, 2H), 1.64~1.66 (m, 5H), 1.45~1.48 (m, 4H), 1.23~1.40 (m, 18H), 1.08~1.15 (m, 6H), 0.79~0.86 (m, 2H). 13C NMR (DMSO-$d_6$) δ (ppm): 37.06, 36.99, 32.9, 30.0 (d, $^3J_{C-P}$=15.9 Hz), 29.4, 29.1, 28.9, 28.7, 26.9 (d, $^1J_{C-P}$=135.7 Hz), 26.3, 26.2, 25.9, 22.7 (d, $^2J_{C-P}$=4.2 Hz). HRMS (API+) Calcd. for $C_{18}H_{37}O_3P$ $[M+H]^+$: 333.2553. Found: 333.2549.

Formation of Self-Assembled Monolayers (SAMs) of CDPA on a Dielectric Oxide

In the manner of Su et al., *ACS Appl. Mater. Interfaces* 2011, 3, 4662-67, a heavily n-doped Si wafer ($n^{++}$-Si) as a gate electrode was ultrasonically cleaned by acetone, isopropanol and ethanol, in succession, and then used immediately for spin-coating after being blown dry with $N_2$ gas. A TiOx layer was deposited by spin-coating a $TiO_x$ sol onto the cleaned $n^{++}$-Si substrates at 5000 r/min for 40 s, followed by baking at 200° C. for 5 min to ensure the hydrolyzation and decomposition of the precursor. The titanium oxide ($TiO_x$) sol was prepared by dissolving titanium(IV) isopropoxide (TIP) ($Ti(OC_3H_7)_4$) into a mixture of methanol and acetic acid in a concentration of about 0.1 mol/L, and vigorously stirring for 24 h under ambient conditions. Subsequently, the $Al_2O_y$ layer was deposited by spin-coating the $Al_2O_y$ sol onto the cooled $TiO_x$-coated substrates and then baked at the same condition as that employed for the $TiO_x$ layer. The Aluminum oxide ($Al_2O_y$) sol was prepared by dissolving aluminum nitrate nonahydrate ($Al(NO_3)_3 \cdot 9H_2O$ in 2-methoxyethanol at a concentration of about 0.5 mol/L and then stirring for 12 h under ambient conditions. To form SAMs of CDPA, the $AlO_y/TiO_x$-coated Si wafer was soaked in a solution of CDPA in isopropanol (0.5 mg/mL) at room temperature for 12 hours, and then rinsed with isopropanol and dried with a flow of nitrogen. This CDPA-modified $AlO_y/TiO_x$ displayed a capacitance per unit area of 210±18 $nF/cm^2$.

Fabrication of OTFTs with a CDPA-Modified $AlO_y/TiO_x$ Dielectric

Vacuum-Deposited OTFTs

A thin film of an organic semiconductor was deposited on the CDPA-modified $AlO_y/TiO_x$ dielectric using an Edwards Auto 306 vacuum coating system at a pressure of 2.0×10⁶ torr or lower, with a deposition rate of ca. 0.1 nm/s to a thickness of 40 nm, as measured by a quartz crystal sensor. Top contact drain and source gold electrodes (ca. 20 nm thick) were vacuum-deposited through a shadow mask onto the organic films using the Edward Auto 306 vacuum coating system. Semiconducting channels of 50 μm (L)×1 mm (W), 100 μm (L)×1 mm (W), 150 μm (L)×1 mm (W), 50 μm (L)×2 mm (W) and 100 μm (L)×2 mm (W) were prepared.

Solution-Processed OTFTs

A solution of an organic semiconductor (0.5 mg/mL for TIPS-PEN and H-NDI or 0.25 mg/mL for TIPS-TAP) in dichloromethane and acetone (1:1) was dropped onto the CDPA-modified $AlO_y/TiO_x$ dielectric and the solvent was evaporated in air to yield a thin film of the semiconductor. The devices were subsequently placed in a vacuum oven overnight to completely remove solvent residues. Top contact drain and source gold electrodes were vacuum-deposited through a shadow mask onto the films by the Edward Auto 306 vacuum coating system at a pressure of 2.0×10⁶ torr or lower, with a deposition rate of ca. 2 nm/min to a thickness about 20 nm, as measured by a quartz crystal sensor. Semiconducting channels of 50 μm (L)×1 mm (W), 100 μm (L)×1 mm (W), 150 μm (L)×1 mm (W), 50 μm (L)×2 mm (W) and 100 μm (L)×2 mm (W) were prepared.

Figure 4:
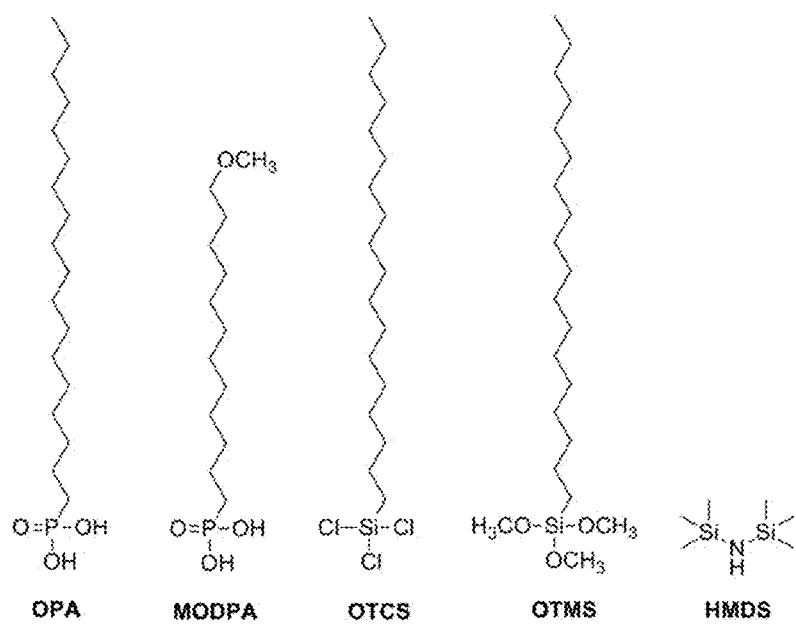
FIG. 4 shows prior art agents used for the formation of SAMs of OTFTs, for comparison to the performance of OTFTs according to an embodiment of the invention.

For comparison of OTFT properties, literature values for field effect mobilities reported for OTFTs employing prior art SAM layers of octadecylphosphonic acid (OPA), 12-methoxydodecylphosphonic acid (MODPA), octadecyltrichlorosilane (OTCS), octadecyltrimethoxysilane (OTMS), and hexamethyldisilazane (HMDS), whose structures are shown in FIG. 4, and those of the OTFTs, according to embodiments of the invention, are given in Tables 2 and 3, below. These alternative prior art SAM formers are not universally useful in high mobility p- and n-channel OTFTs fabricated using either vacuum deposition or solution processing to deposit the organic semiconductor. In the case of OTCS and OTMS, OTFTs by solution processing is not possible, n-channel devices exhibit relatively poor stability in air, and are sensitive to water. In the case of OPA, solution processed OTFTs do not demonstrate high field effect mobilities. In the case of MODPA, though vacuum deposition and solution processing provide high field effect mobilities, mobilities and air stability are inferior to those of the OTFTs using CDPA. In the case of HMDS, high mobilities are not possible with n-channel OTFTs, and HMDS does not display a long shelf life as does CDPA.

mobility measurement was carried out under vacuum, air, nitrogen, or argon as indicated, where values are from the references below.

TABLE 3

Field effect mobilities ($cm^2V^{-1}s^{-1}$) of solution-processed OTFTs that were fabricated on different dielectric surfaces.

| Organic Semiconductor | CDPA-modified $AlO_y/TiO_x$ | MODPA-modified $AlO_y/TiO_x$ | HMDS-modified $SiO_2$ |
|---|---|---|---|
| TIPS-PEN (p-type) | 1.1~2.8 (air) | 1.0~1.5 (air)[6] | 0.2~1.8 (air)[8] |
| TIPS-TAP (n-type) | 1.3~5.0 (vacuum) 0.18~1.7 (air) | 1.1~2.5 (vacuum)[6] 0.02 (air)[6] | 0.005 (vacuum)[6] |
| H-NDI (n-type) | 0.48~1.0 (vacuum) 1.0~1.9 (air) | 0.39~0.59 (vacuum) 0.011~0.054 (air) | | mobility measurement was carried out under vacuum or air as indicated, where values are from the references below.

[1] Ito et al., *J. Am. Chem. Soc.* 2009, 131, 9396-404.
[2] Tang et al., *Chem. Mater.* 2009, 21, 1400-5.
[3] Chung et al. *Nano Lett.* 2011, 11, 1161-5.
[4] Tang et al. *Chem. Commun.* 2010, 46, 2977-9.
[5] Shukla et al., *Chem. Mater.* 2008, 20, 7486-8491.
[6] Liu et al., *Angew. Chem. Int. Ed.*, 2013, 52, 6222-7.
[7] Liang et al., *Adv. Mater.* 2011, 23, 1535-1539.
[8] Park et al., *Appl. Phys. Lett.* 2007, 91, 063514.

Additional Formation of $AlO_y/TiO_x$ and SAMs

A thin layer of $AlO_y/TiO_x$ was spin-coated onto a highly doped silicon substrate with an area of ca. 1 cm×1 cm and resistivity smaller than 0.005 Ωcm following the solution-based procedure to form dielectrics of Su et al., *ACS Appl. Mater. Interfaces* 2011, 3, 4662-67. To form SAMs of phosphonic acids, an $AlO_y/TiO_x$-coated Si wafer was treated with oxygen plasma for two minutes and then soaked in a solution of the corresponding phosphonic acid in isopropyl alcohol (1.5 mM) at room temperature for 12 hours, and then rinsed with isopropyl alcohol and dried with a flow of nitrogen.

Measurement of Surface Energy

Static contact angle between a drop of probe liquid and a SAM was measured with a contact angle goniometer, and distilled water and diiodomethane ($CH_2I_2$) were used as the probe liquid. The dispersion and polar components of the surface energy were calculated using the equation:

$$(1+\cos\theta)\gamma_l = (\gamma_s^D \gamma_l^D)^{1/2} + 2(\gamma_s^P \gamma_l^P)^{1/2}$$

TABLE 2

Field effect mobilities ($cm^2V^{-1}s^{-1}$) of n-channel OTFTs that were fabricated on different dielectric surfaces.

| Organic Semiconductor | CDPA-modified $AlO_y/TiO_x$ | OPA-modified $AlO_x$ or $AlO_y/TiO_x$ | OTCS-modified $SiO_2$ | OTMS-modified $SiO_2$ |
|---|---|---|---|---|
| Pentacene (p-type) | 3.1~5.7 (air) | | 0.52 ± 0.04 (air)[1] 0.68~0.82 (air)[2] | 2.8 ± 0.2 (air)[1] |
| $C_{60}$ (n-type) | 2.4~5.5 (vacuum) 1.8~5.1 (air) | 1.69 ± 0.14 (air)[3] | 0.27 ± 0.15 ($N_2$)[1] | 4.7 ± 0.41 ($N_2$)[1] |
| TAPQ (n-type) | 0.78~1.5 (vacuum) 0.13~0.22 (air) | | | 0.04~0.12 (vacuum)[4] 0.002 (air)[4] |
| C-NDI (n-type) | 1.6~1.8 (vacuum) 1.2~3.0 (air) | | 4.5~6.5 (Ar)[5] 0.41 (air)[5] | |
| TIPS-TAP (n-type) | 1.1~1.7 (vacuum) 0.50~1.2 (air) | 1.3~1.8 (vacuum)[6] 0.35 (air)[6] | | 1.0~3.3 (vacuum)[7] 0.3~0.5 (air)[7] |

Here θ is the equilibrium contact angle made by each liquid on the solid surface, γ is the surface energy. The superscripts D and P refer to the dispersive and the polar components, respectively, and the subscripts l and s refer to the liquid and solid, respectively. The dispersion and polar components of the surface tension are 21.8 mN m$^{-1}$ and 50.9 mN m$^{-1}$, respectively, for water, and 50.0 mN m$^{-1}$ and 0 mN m$^{-1}$, respectively, for CH$_2$I$_2$.

Measurement of Capacitance and Leakage Current

The capacitance of SAM-modified AlO$_y$/TiO$_x$ was measured in a frequency range of 100 Hz to 100 kHz from a metal-insulator-metal structure, which had vacuum-deposited gold (0.2 mm×1 mm) as the top electrode and a highly doped silicon substrate as the bottom electrode. The average capacitance per unit area ($C_i$) of SAM-AlO$_y$/TiO$_x$ was taken at the lowest frequency (100 Hz). The leakage current was measured from the same metal-insulator-metal structure with a voltage of −3 V to 3 V.

Fabrication and Characterization of OTFTs

Thin films of pentacene and C$_{60}$ were vacuum-deposited onto the SAM-modified AlO$_y$/TiO$_x$ using an Edwards Auto 306 vacuum coating system at a pressure of 2.0×10$^{-6}$ Torr or lower, with a deposition rate of ca. 1 Å s$^{-1}$ to a thickness of 40 nm as measured by a quartz crystal sensor. During vacuum deposition the distance between source and substrate was 18.5 cm, and the substrate was kept at 60° C. for pentacene and 90° C. for C 60 by heating with a radiant heater. Thin films of TIPS-PEN and TIPS-TAP were formed by dropping a 0.5 mg/mL solution in a mixed solvent of dichloromethane and acetone (a volume ratio of 1:1) onto the CDPA-modified AlO$_y$/TiO$_x$. The drop-cast films were placed in a vacuum oven overnight to completely remove solvent residues. A layer of gold was deposited through a shadow mask onto the organic films to form top-contact source and drain electrodes. The resulting devices had highly doped silicon as the gate electrode and the SAM-modified AlO$_y$/TiO$_x$ as dielectrics. The field effect mobility of these OTFT in the saturation regime is extracted from transfer I-V curves using the equation:

$$I_{DS}=(\mu W C_i/2L)(V_G-V_T)^2,$$

where $I_{DS}$ is the drain current, μ is field-effect mobility, $C_i$ is the capacitance per unit area for the SAM-modified AlO$_y$/TiO$_x$, W is the channel width, L is the channel length, and $V_G$ and $V_T$ are the gate and threshold voltage, respectively. To obtain average values, at least 20 channels on five substrates were tested for each condition.

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A cycloalkylalkylphosphonic acid or dialkyl cycloalkylalkylphosphonate ester, of the structure:

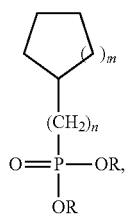

where n is 6-20, m is 1 to 4, and R is hydrogen, methyl, ethyl, or propyl.

2. The cycloalkylalkylphosphonic acid or dialkyl cycloalkylalkylphosphonate ester according to claim 1, wherein the cycloalkylalkylphosphonic acid is 12-cyclohexyldodecylphosphonic acid (CDPA).

3. The cycloalkylalkylphosphonic acid or dialkyl cycloalkylalkylphosphonate ester according to claim 1, wherein the dialkyl cycloalkylalkylphosphonate ester is diethyl-12-cyclohexyldodecylphosphonate.

4. A method of preparing a cycloalkylalkylphosphonic acid, according to claim 1, comprising:
   providing a halogen substituted cycloalkane;
   forming a cycloalkylmagnesium halide from the halogen substituted cycloalkane;
   combining the cycloalkylmagnesium halide with an α,ω-dihalogen substituted n-alkane to form an α-halo-ω-cycloalkylalkane;
   combining the α-halo-ω-cycloalkylalkane with a trialkyl phosphite to form a dialkyl cycloalkylalkylphosphonate ester, according to claim 1;
   combining the dialkyl cycloalkylalkylphosphonate ester with trimethylsilicon bromide in a first step and with water in a second step to form a cycloalkylalkylphosphonic acid; wherein the cycloalkane is cyclopentane, cyclohexane, cycloheptane, or cyclooctane; wherein the halogen and dihalogen are independently Cl, Br, or I; wherein the n-alkane is n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, or n-icosane; and wherein the trialkyl phosphite is trimethyl phosphite, triethyl phosphite, or tripropyl phosphite.

5. The method according to claim 4, wherein the cycloalkane is cyclohexane, the halogen is Br, the n-alkane is n-dodecane, and the trialkyl phosphite is triethyl phosphite.

6. A self-assembled monolayer (SAM), comprising cycloalkylalkylphosphonic acid according to claim 1 disposed on a surface.

7. The self-assembled monolayer (SAM) according to claim 6, wherein the cycloalkylalkylphosphonic acid is 12-cyclohexyldodecylphosphonic acid (CDPA).

8. The self-assembled monolayer (SAM) according to claim 6, further comprising a metal oxide layer having the surface.

9. The self-assembled monolayer (SAM) according to claim 8, wherein the metal oxide of the metal oxide layer is aluminum oxide, titanium oxide, zirconium oxide, planar mica, silica, zinc oxide, copper oxide, nickel oxide, tantalum oxide, hafnium oxide, iron oxide, chromium oxide, niobium oxide, zirconium oxide, or any mixed metal oxide thereof.

10. The self-assembled monolayer (SAM) according to claim 8, wherein the metal oxide of the metal oxide layer is AlO$_y$/TiO$_x$.

* * * * *

UNITED STATES PATENT AND TRADEMARK OFFICE
CERTIFICATE OF CORRECTION

PATENT NO. : 9,701,698 B2
APPLICATION NO. : 14/729592
DATED : July 11, 2017
INVENTOR(S) : Qian Miao, Danqing Liu and Zikai He It is certified that error appears in the above-identified patent and that said Letters Patent is hereby corrected as shown below:

In the Specification

Column 5, Line 33,
"(e) are known" should read --($\sigma$*) are known--.

Column 6, Lines 59-61,
"0.23 ± 0.07 cm2 V–1 s–1 (measured in air) and (7.3 ± 0.6) × 10–3 cm2 V–1 s–1 (measured in vacuum)" should read --0.23 ± 0.07 $cm^2$ $V^{-1}$ $s^{-1}$ (measured in air) and (7.3 ± 0.6) × 10–3 $cm^2$ $V^{-1}$ $s^{-1}$ (measured in vacuum)--.

Column 7, Line 2,
"1.09 ± 0.26 cm2 V–1 s–1, respectively" should read --1.09 ± 0.26 $cm^2$ $V^{-1}$ $s^{-1}$, respectively--.

Column 7, Line 24,
"C60 (4.7 ± 0.41 $cm^2$ $V^{-1}$ $s^{-1}$" should read --$C_{60}$ (4.7 ± 0.41 $cm^2$ $V^{-1}$ $s^{-1}$--.

Column 10, Line 42,
"A TiOx layer" should read --A $TiO_x$ layer--.

Column 13, Line 29,
"for C 60 by heating" should read --for $C_{60}$ by heating--.

Signed and Sealed this
Twenty-seventh Day of March, 2018

Andrei Iancu
*Director of the United States Patent and Trademark Office*